(12) United States Patent
Sabra

(10) Patent No.: US 7,470,250 B2
(45) Date of Patent: Dec. 30, 2008

(54) APPARATUS FOR AUTOMATIC INSERTION OF A SOLID MEDICINE

(75) Inventor: Mads Christian Sabra, Kobenhavn N (DK)

(73) Assignee: Novo Nordisk A/S, Bagsvaerd (DK)

( * ) Notice: Subject to any disclaimer, the term of this patent is extended or adjusted under 35 U.S.C. 154(b) by 189 days.

(21) Appl. No.: 10/390,981

(22) Filed: Mar. 18, 2003

(65) Prior Publication Data
US 2003/0225367 A1 Dec. 4, 2003

Related U.S. Application Data

(60) Provisional application No. 60/374,456, filed on Apr. 5, 2002.

(51) Int. Cl.
*A61M 31/00* (2006.01)
(52) U.S. Cl. ...................................... 604/63
(58) Field of Classification Search ........... 604/57–604, 604/15–16
See application file for complete search history.

(56) References Cited

U.S. PATENT DOCUMENTS

| | | | | |
|---|---|---|---|---|
| 2,007,626 A | * | 7/1935 | Waring | 604/59 |
| 2,632,444 A | * | 3/1953 | Kas | 604/62 |
| 3,072,121 A | * | 1/1963 | Feldmann | 604/57 |
| 4,276,878 A | | 7/1981 | Storz | 128/218 |
| 4,769,011 A | * | 9/1988 | Swaniger | 604/218 |
| 5,279,555 A | * | 1/1994 | Lifshey | 604/60 |
| 5,542,920 A | * | 8/1996 | Cherif Cheikh | 604/57 |
| 5,772,671 A | * | 6/1998 | Harmon | 606/117 |
| 6,569,182 B1 | * | 5/2003 | Balceta et al. | 606/200 |
| 2003/0054044 A1 | | 3/2003 | Potter et al. | |
| 2005/0013840 A1 | | 1/2005 | Potter et al. | |

(Continued)

FOREIGN PATENT DOCUMENTS

GB    2 379 390 A    3/2003

(Continued)

OTHER PUBLICATIONS

Office Action issued in connection with counterpart Danish Application No. PA 2002 00444, mailed Oct. 2, 2002.

(Continued)

*Primary Examiner*—Kevin C. Sirmons
*Assistant Examiner*—Catherine N Witczak
(74) *Attorney, Agent, or Firm*—Wesley A. Nicolas; Marc A. Began

(57) ABSTRACT

An apparatus for insertion of a medicine peg (3) into the skin (4) has a barrel (2) wherein the medicine peg (2) is stored and in which a plunger (8) behind said peg (2) can be moved to press the peg out through an end of the barrel (2) pressed against the skin (4) where it is intended to insert the peg (3), The plunger (8) is a part of a flexible rod construction (6, 7, 8) which can be passed from a first non rectilinear constellation, by which the plunger (8) is withdrawn in the barrel (2) to a position leaving space for the medicine peg (3) in front of the plunger (8), to a rectilinear constellation by which the plunger (8) projects from the end of the barrel (2) and further to a new non rectilinear position in which the end of the plunger (8) is withdrawn in the barrel (2).

3 Claims, 1 Drawing Sheet

U.S. PATENT DOCUMENTS

2006/0161111 A1    7/2006   Potter et al.

FOREIGN PATENT DOCUMENTS

WO      01/68168      9/2001

OTHER PUBLICATIONS

International Search Report issued in connection with counterpart International Application No. PCT/DK03/00149, mailed May 27, 2003.

International Preliminary Examination Report issued in connection with counterpart International Application No. PCT/DK03/00149, mailed Jan. 8, 2004.

\* cited by examiner

APPARATUS FOR AUTOMATIC INSERTION OF A SOLID MEDICINE

CROSS-REFERENCE TO RELATED APPLICATIONS

This application claims priority under 35 U.S.C. 119 of Danish application PA 2002 00444 filed Mar. 22, 2002 and U.S. provisional application No. 60/374,456 filed Apr. 5, 2002, the contents of which are fully incorporated herein by reference.

The invention relates to an apparatus for automatic insertion of medicine pegs into the skin.

BACKGROUND OF THE INVENTION

Some medicaments are injected as heavy soluble crystals or particles suspended in a solvent. When injected the heavy soluble medicine is during time dissolved by the tissue liquid. Instead of suspending or dissolving the medicine in a solvent the dry medicine may be pressed to a small needle shaped peg which can be inserted into the tissue from where it is during time dissolved by the tissue liquid.

From U.S. Pat. No. 5,542,920 is known a device by which a peg stored in a barrel which is provided in a housing and from which said peg can be pressed into the skin by a plunger which can be passed into the barrel by pressing a button. Alternatively the peg can be shot into the skin by a spring or by applying a gas pressure behind the peg in the barrel.

When the peg is pressed into the skin by a plunger which is pressed into the barrel from one end thereof whereas the other end of the barrel is pressed against the skin where the insertion is wanted, the plunger must be pressed to a position where its end facing the peg is passed some millimetres into the skin to ensure that the peg is inserted to a subcutaneous position. Thereafter it is wanted to have the plunger drawn back into the barrel so that the end of the plunger, which may have been contaminated by the insertion, is hidden in the barrel. This may be obtained by providing a spring between the housing and the button by which the plunger is pressed into the barrel. By the insertion movement of the button this spring is compressed and when the button is released said spring will press the button back and this way draw the plunger back from its peg insertion position leaving the peg subcutaneously inserted.

It is an objective of the invention to provide a small handy device by which a solid medicine peg may be automatically inserted.

SUMMARY OF THE INVENTION

This is obtained by an apparatus for automatic insertion of medicine pegs into the skin which apparatus has a barrel in which a medicine peg is stored and in which a plunger behind said peg can be moved to press the peg out through an end of the barrel which end is pressed against the skin on the location where the peg is intended to be inserted, which apparatus is according to the invention characterised in that the plunger is a part of a flexible rod construction which is so designed that it can be passed from a first non rectilinear constellation, by which the plunger is withdrawn in the barrel to a position leaving space for the medicine peg, to a rectilinear constellation by which the plunger projects from the end of the barrel.

According to the invention the rod constellation may be a single flexible bar having a first and a second end, said first end being fixed in the housing an said second end being placed behind a medicine peg in the barrel, which flexible bar between said first and second ends has a deflection in a first direction perpendicular to its axis, spring mechanisms being provided which act on the deflection in a direction to straighten the deflection and provide a deflection in a second direction opposite said first direction.

The spring mechanism may be provided by an inherent spring force in the flexible bar which is formed with a deflection in said second direction and against its inherent spring force is forced to have a deflection in said first direction.

The bar is held in its position with a deflection in said first direction until a release mechanism is activated to set free the spring forces which will force the bar over a rectilinear position to a position with a deflection in said second direction. When the bar is moving towards its rectilinear position, the end of the bar which forms a plunger will press the medicine peg out of the barrel and into the skin when the outer end of the barrel is pressed against the skin. When the bar reaches its rectilinear position, the plunger projects a short distance from the end of the barrel whereby it is ensured that the peg is pressed to a position the same distance under the skin surface. By the further movement of the bar to its position with a deflection in the second direction, the end of the plunger is withdrawn from the skin so that the device can be removed from its contact with the skin without any risk of scratching.

In another embodiment the spring mechanism may comprise a spring provided and compressed between the housing and the flexible rod when this rod is in its first non rectilinear position, so that the spring presses the flexible rod towards its rectilinear position.

In another embodiment the flexible rod constellation may be formed by three rectilinear rods which are through links coupled in series so that one rod forms the plunger whereas a knee link mechanism is formed by a first rod linked between the plunger and a second rod, which is linked between the first rod and a point in the housing which point lies on the extension of the plunger rod axis. A spring act on the knee link mechanism where the first rod is coupled to the second rod in a direction so that a straightening of the knee link is attempted. When the knee link is straightened the peg is pressed out of the barrel and the plunger project a short distance from the end of the barrel. When the further action of the spring moves the knee link mechanism to a new bent position the plunger is drawn back into the barrel.

During the movement from its initial position to its final position the second rod rotates about a pin fixed in the housing. It may be attractive to provide a fly wheel which can help said second rod in its rotation towards its final position. This can be obtained by replacing the second rod by a disk rotating about said pin fixed in the housing. The rotation of the disk can be supported by a spring acting on the disk to provide a torque about said pin.

The rod constellation described has the advantage that it provides in a very simple way a gearing transforming a movement provided by a small force, the movement of the deflection provided by the spring mechanism, to a shorter movement with a stronger force, the movement of the plunger which presses the peg into the skin.

In the following the invention is further described with references to the drawing, wherein

DETAILED DESCRIPTION

Figures 1, 2, 3:
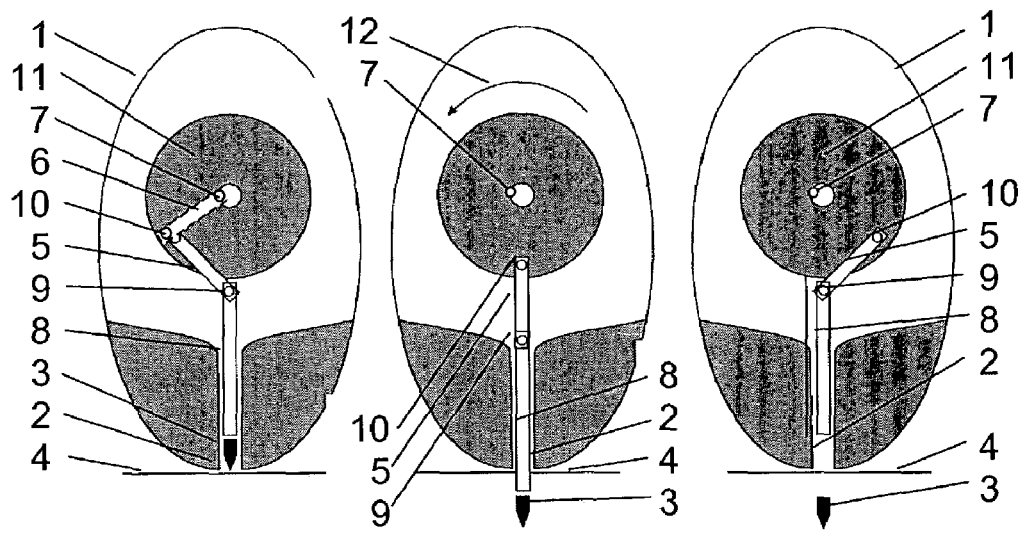
FIG. 1 shows schematically a device according to the invention with its rod constellation in its initial non rectilinear position.
FIG. 2 shows the device in figure with its rod constellation in its rectilinear position.
FIG. 3 shows the device of FIGS. 1 and 2 with its rod constellation in its final non rectilinear position.

In FIG. 1 is a housing 1 provided with a barrel 2 in which a peg 3 of solid medicine is placed at the outlet of the barrel 2 ready to be passed through the skin 4 of a patient. In the barrel 2 behind the peg 3 a rod shaped plunger 8 is placed which plunger by a first (5) and a second rod (6) rod is connected to a pivot pin 7 in the housing 1. The first rod 5 is at its one end coupled to an inner end of the plunger by a link 9 and at its other end coupled to the second rod 6 by a link 10. The lengths of the plunger 8 and the rods 5 and 6 are so adjusted that they form a knee link mechanism between the pin 7 and the inner end of the plunger 8 when said plunger is in its position behind a peg 3 in the barrel 2. The second rod 6 can be rotated about the pivot pin 7 and this rotation can be supported by a flywheel 11 into which the second rod can be integrated as shown in FIGS. 2 and 3.

In FIG. 2 the flywheel 11 has been rotated so far in the direction indicated by the arrow 12 that the plunger 8, the links 9 and 10, and the pivot pin 7 lies on one straight line, i.e. the rods of the knee link mechanism and the plunger are brought to a rectilinear position. The lengths of the plunger and the first and the second rods are so adjusted that the plunger in this position projects from the outer end of the barrel a short distance. Thereby it is ensured that the peg 3 is positioned a short distance beneath the surface of the skin 4. The distance is set by the choice of the lengths of the rods 5 and 6 and the plunger 8. The length of the integrated second rod is defined by the distance between the pivot pin 7 and the link 10.

In FIG. 3 the flywheel 11 and its integrated second rod has been further rotated to a position wherein the plunger 8 and the first and the second rod does no longer attain a rectilinear constellation. Thereby the plunger 8 is withdrawn from its position projecting from the barrel 2 and leaves the peg 3 a suitable distance beneath the skin 4.

The device can be a disposable device wherein the rotation of the second rod 6 and the flywheel is induced by a not shown spring working between the housing and the flywheel 11 or the second rod 6. When the device is stored it will be in the position shown in FIG. 1 with the spring cocked. When the apparatus is going to be used the opening of the barrel is pressed against the skin and the cocked spring is released. Thereby the second rod is rotated in the direction shown by the arrow 12 in FIG. 2. The rod is rotated through the position shown in FIG. 2 to the position shown in FIG. 3 where the plunger is drawn back into the barrel. Hidden in the barrel the plunger, which may be contaminated by the perforation of the skin, cannot get in touch with anybody.

Figures 4, 5, 6:
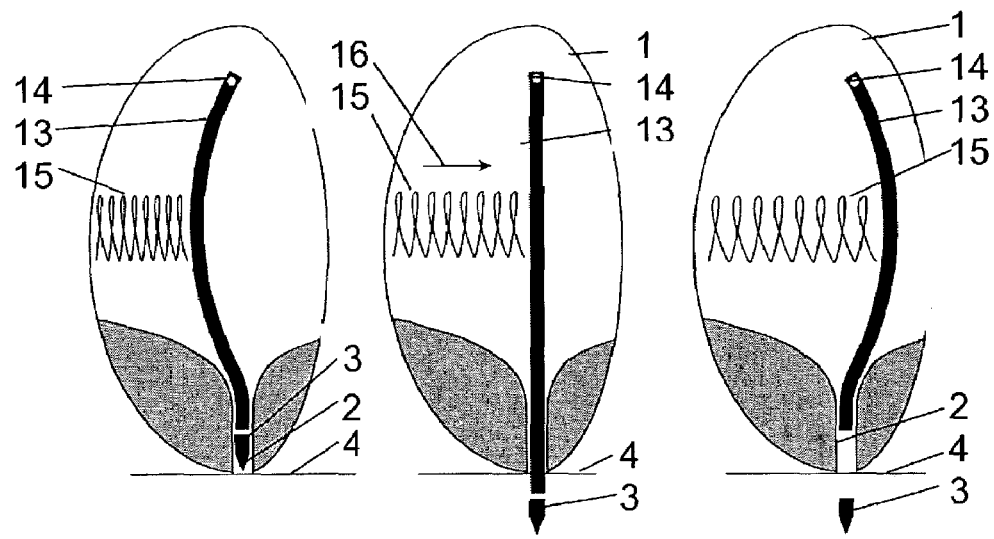
FIG. 4 shows schematically another embodiment of a device according to the invention wherein the rod constellation is represented by one integral flexible rod in an initial non rectilinear position.
FIG. 5 shows the device of FIG. 4 with the rod in its rectilinear position.
FIG. 6 shows the device of FIGS. 4 and 5 with the rod in its final non rectilinear position.

FIGS. 4, 5, and 6 shown another embodiment of a device according to the invention. In this embodiment the plunger rod and the first and second rod of the knee link mechanism is replaced by one single flexible rod 13 which is at one end guided in the barrel 2 and is at the other end rotatably fixed in the housing by a pin 14. The flexible rod can be a rectilinear rod which is in FIG. 1 held in a bent out position in which the free end of the rod 13 is positioned a distance from the mouth of the barrel 2 allowing a peg to be placed in this barrel adjacent to the mouth thereof.

When the rod 13 is released it will pass to a rectilinear position either by its own inherit spring force or by the force of a spring 15 acting on the rod perpendicular to its axis between the free end and the end fixed in the housing 1. From its rectilinear position the flexible rod will further move in the direction shown by an arrow 16 in FIG. 5 to a new bent out position shown in FIG. 6 in which said rod is withdrawn from its projecting position.

I claim:

1. An apparatus for automatic insertion of a medicine peg into the skin comprising:

a barrel wherein a medicine peg is stored, and a plunger structured for movement within the barrel, the plunger being structured to drive the peg into the skin, wherein the plunger is, at least in part, flexible and wherein the plunger is structured to drive the peg by moving from a first resting non-rectilinear constellation before administration of the peg, to a second rectilinear constellation upon administration of the peg, and then to a third resting non-rectilinear position that is substantially symmetrical about the longitudinal axis of the rectilinear constellation with the first resting non-rectilinear position, and wherein movement to the third resting non-rectilinear position retracts the plunger from at least part of the barrel.

2. The apparatus according to claim 1, wherein a spring is provided and cocked between a housing and the plunger when the plunger occupies the first resting non rectilinear constellation, so that when the spring is uncocked, the spring is structured to move the plunger to the second rectilinear constellation thereby driving the peg into the skin.

3. The apparatus of claim 2, further comprising a mechanism to release the cocked spring thereby automatically driving the peg into the skin.

* * * * *